US012024698B2

(12) United States Patent
Corso et al.

(10) Patent No.: US 12,024,698 B2
(45) Date of Patent: Jul. 2, 2024

(54) SYSTEM, DEVICE AND METHOD FOR ELECTROPORATION OF CELLS

(71) Applicant: CyteQuest, Inc., Ithaca, NY (US)

(72) Inventors: Thomas N. Corso, Groton, NY (US); Harold G. Craighead, Ithaca, NY (US)

(73) Assignee: CyteQuest, Inc., Ithaca, NY (US)

( * ) Notice: Subject to any disclaimer, the term of this patent is extended or adjusted under 35 U.S.C. 154(b) by 23 days.

(21) Appl. No.: 17/519,778

(22) Filed: Nov. 5, 2021

(65) Prior Publication Data

US 2022/0056392 A1 Feb. 24, 2022

Related U.S. Application Data

(63) Continuation of application No. 15/478,924, filed on Apr. 4, 2017, now Pat. No. 11,225,638.

(60) Provisional application No. 62/318,022, filed on Apr. 4, 2016.

(51) Int. Cl.
| | |
|---|---|
| *C12M 1/42* | (2006.01) |
| *C12M 1/02* | (2006.01) |
| *C12M 1/34* | (2006.01) |
| *C12N 13/00* | (2006.01) |
| *C12N 15/87* | (2006.01) |

(52) U.S. Cl.
CPC ............ *C12M 35/02* (2013.01); *C12M 27/00* (2013.01); *C12M 41/46* (2013.01); *C12N 13/00* (2013.01); *C12N 15/87* (2013.01)

(58) Field of Classification Search
None
See application file for complete search history.

(56) References Cited

U.S. PATENT DOCUMENTS

| | | | |
|---|---|---|---|
| 4,752,586 | A | 6/1988 | Ropars et al. |
| 5,612,207 | A | 3/1997 | Nicolau et al. |
| 6,074,605 | A | 6/2000 | Meserol et al. |
| 6,090,617 | A | 7/2000 | Meserol |
| 6,482,619 | B1 | 11/2002 | Rubinsky et al. |

(Continued)

FOREIGN PATENT DOCUMENTS

| | | |
|---|---|---|
| CN | 101928666 B | 4/2013 |
| JP | 2006/197872 A | 8/2006 |

(Continued)

OTHER PUBLICATIONS

Majhi et al. "Optically transparent polymer devices for in situ assessment of cell electroporation", Eur Biophys J (2015) 44:57-67. (Year: 2015).*

(Continued)

*Primary Examiner* — William H. Beisner
(74) *Attorney, Agent, or Firm* — Foley Hoag LLP; Dana M. Gordon

(57) ABSTRACT

A system, device and method for electroporation of living cells and the introduction of selected molecules into the cells utilizes a fluidic system where living cells and biologically active molecules flow through a channel that exposes them to electric fields, causing the molecules to be transferred across the cell membrane. The device is structured in a manner that allows precise control of the cells location, motion, and exposure to electric fields within the flow channel device. The method is particularly well suited for the introduction of DNA, RNA, drug compounds, and other biologically active molecules into living cells.

17 Claims, 7 Drawing Sheets

(56) References Cited

U.S. PATENT DOCUMENTS

| | | |
|---|---|---|
| 6,653,136 B1 | 11/2003 | Dodgson et al. |
| 6,773,699 B1 | 8/2004 | Soltz et al. |
| 7,131,325 B2 | 11/2006 | Nilsson et al. |
| 7,141,425 B2 | 11/2006 | Dzekunov et al. |
| 7,771,984 B2 | 8/2010 | Dzekunov et al. |
| 8,222,909 B2 | 7/2012 | Ragsdale |
| 11,225,638 B2 | 1/2022 | Corso et al. |
| 2002/0058019 A1 | 5/2002 | Berenson et al. |
| 2003/0044832 A1 | 3/2003 | Blankenstein |
| 2003/0075446 A1 | 4/2003 | Culbertson et al. |
| 2004/0106189 A1 | 6/2004 | Dodgson et al. |
| 2006/0121446 A1 | 6/2006 | Abassi et al. |
| 2006/0134067 A1 | 6/2006 | Liu et al. |
| 2009/0281477 A1 | 11/2009 | Mikus et al. |
| 2012/0190040 A1 | 7/2012 | Talebpour et al. |
| 2012/0225424 A1 | 9/2012 | Abassi et al. |
| 2012/0276635 A1* | 11/2012 | Lu ................... C12M 47/06 435/173.6 |
| 2013/0052711 A1 | 2/2013 | Chen |
| 2014/0066836 A1 | 3/2014 | Cancedda et al. |
| 2014/0113356 A1 | 4/2014 | Tseng et al. |
| 2014/0170646 A1 | 6/2014 | Kelley et al. |
| 2014/0287509 A1 | 9/2014 | Sharei et al. |
| 2017/0283761 A1 | 10/2017 | Corso |
| 2018/0258379 A1 | 9/2018 | Zahn et al. |
| 2019/0100721 A1 | 4/2019 | Bernate et al. |
| 2019/0119624 A1 | 4/2019 | Tandon et al. |
| 2020/0318055 A1 | 10/2020 | Dai |
| 2020/0332276 A1 | 10/2020 | Buie et al. |
| 2020/0399578 A1 | 12/2020 | Corso et al. |
| 2021/0284948 A1 | 9/2021 | Hauwaerts et al. |
| 2023/0109873 A1 | 4/2023 | Corso et al. |
| 2023/0114435 A1 | 4/2023 | Corso et al. |

FOREIGN PATENT DOCUMENTS

| | | |
|---|---|---|
| KR | 100807852 B1 | 2/2008 |
| WO | WO-2020/232437 A1 | 11/2020 |
| WO | WO-2023/064444 A1 | 4/2023 |
| WO | WO-2023/064456 A1 | 4/2023 |

OTHER PUBLICATIONS

Burgel, Sebastian C., et al., "On-chip electroporation and impedance spectroscopy of single-cells," Sensors and Actuators B: Chemical, vol. 210, Dec. 17, 2014, pp. 82-90.

Chang, Lingqian, et al., "Micro-/nanoscale electroporation," Lab on a Chip, vol. 16, No. 21, Sep. 19, 2016, pp. 4047-4062.

Cho et al., "A high throughput microelectroporation device to introduce a chimeric antigen receptor to redirect the specificity of human T cells," Biomed Microdevices, 12(5):855-863 (2010).

International Search Report and Written Opinion Form PCT/ISA/220, International Application No. PCT/US2017/025956, pp. 1-9, International filing Date Apr. 4, 2017, mailing date of search.

International Search Report and Written Opinion Form PCT/ISA/237, International Application No. PCT/US2017/025956, pp. 1-9, International Filing Date Apr. 4, 2017.

Lin et al., "Electroporation microchips for continous gene transfection," Sensors and Actuators B, vol. 79 (2001), pp. 137-143. (Year: 2001).

Supplementary European Search Report for European Applicaion No. 17779655; date of completion of search Oct. 31, 2019.

Wei et al., "A Laminar Flow Electroporation System for Efficient DNA and siRNA Delivery," Anal. Chem., vol. 83 (2011), pp. 5881-5887. (Year: 2011).

International Search Report and Written Opinion for International Application No. PCT/US2020/033401 dated Aug. 28, 2020.

Lin et al., "Electroporation microchips for continuous gene transfection," Sensors and Actuators B, 79:137-143 (2001).

International Search Report and Written Opinion for International Application No. PCT/US22/46531 dated Jan. 13, 2023.

International Search Report and Written Opinion for International Application No. PCT/US2022/046549 dated Jan. 9, 2022.

Extended European Search Report for EP Application No. 20806475.8 dated Jun. 21, 2023.

* cited by examiner

SYSTEM, DEVICE AND METHOD FOR ELECTROPORATION OF CELLS

CROSS REFERENCES

This application is a Continuation of U.S. application Ser. No. 15/478,924, filed Apr. 4, 2017; which claims the benefit of the filing date of U.S. Provisional Patent Application Ser. No. 62/318,022 filed Apr. 4, 2016.

FIELD

The present disclosure relates to methods of molecular biology, and more specifically a system, device, and method for the electroporation of cells.

BACKGROUND OF THE INVENTION

In medicine and biomedical research, there is motivation to insert biologically active molecules into selected living cells. These molecules could be drugs to treat specific diseases, but an important application is the insertion of nucleic acid molecules such as DNA and RNA, which is typically called transfection or transformation. The inserted nucleic acid molecules can serve as a vaccine, can enable the cellular production of specific proteins, or can be used to reprogram the human immune system cells to attack tumors or disease causing cells. In such applications it is critical to insert sufficient DNA or RNA into a cell without doing damage that could kill the cell. Control of the process is important and process parameters generally differ for different types of cells.

A method known as electroporation, or electropermeabilization, has been used for decades as an approach to electrically open pores in cell membranes to allow the passage of molecules into the cells. In this method, electric fields are created by applying high voltage electrical pulses to electrodes inserted in a liquid container containing cells suspended in a liquid solution that contains the molecules to be inserted into the cells. The applied high-voltage pulses create transient pores in the cell membrane that allow molecules to pass into the cells. However, the open pores also allow the cell contents to escape with negative consequences for the health of the cell. The pulse voltage, number of pulses and pulse duration are among the parameters empirically varied to optimize the efficiency of molecular insertion and cell survival. However, current devices are limited in that molecules are exposed to a large range of electric fields, often causing biologically active molecules to not transfer efficiently and/or many cells to be damaged or killed during electroporation. Current devices also lack process variability and cannot be optimized for various cell types and biologically active molecules. Furthermore, current devices have limited throughput. These drawbacks have limited the widespread application of this method.

Some improvement in throughput has been made by flowing a solution with living cells and biologically active molecules through the container with electrodes. For example, a publication by Choi et al. (2010) proposed a high-throughput microelectroporation device for introducing chimeric antigen receptor to human T cells to redirect their specificity. In addition, U.S. Pat. Nos. 4,752,586; 5,612,207; 6,074,605 and 6,090,617 refer to electroporation with flow for processing large number of cells. These devices introduce flow to fill and empty the electroporation chamber, but the living cells are still subjected to various electric fields depending on their distance from the electrodes during flow through the chamber. Thus, the efficiency of molecular transformation as well as the potential lysing of the cells remains a problem.

U.S. Patent Application Publication 2014/0066836, discloses an electroporation device that includes movable electrodes in order to achieve a more specific spatial configuration between the electrodes and the cells. However, the cells reside in a bulk solution in the device or in vivo. Thus, the quantity of cells that are exposed to the precise field strength is limited.

There are also additional practical limitations of the current electroporation methods. For example, high voltages are required and it is often necessary to pulse the voltage in order to allow the cells to recover in between voltage exposure. Also, current devices permit cells to be porated only in a single, homogenous fluid environment. In addition, current devices preclude the ability to optically or electrically monitor the cell motion and electroporation process while it is occurring.

Currently, the art lacks a system, method and device for the introduction of biologically active molecules into flowing living cells by electroporation in a manner that allows control of the living cells' location, motion, local chemical environment and exposure to electric fields.

SUMMARY

In accordance with one aspect of the present disclosure there is provided a device capable of inserting a biologically active molecule into a living cell including a fluid channel including at least one fluid input and a fluid output configured to allow a fluid flow including living cells and biologically active molecules through the channel; and a first electrode and a second electrode on opposite sides of the fluid channel to which electrical potentials can be applied to form an electric field directed across the fluid channel, wherein the distance between the first and second electrodes enables the cells to pass through the space between the electrodes in a single layer so a living cell in the fluid flow is maintained in a similar position as other living cells in the fluid flow as they pass through the electric field between the first and second electrodes in a manner that prevents one living cell from shielding another living cell from the applied electric field, wherein the strength of the electric field to which the living cell is exposed is sufficient to form pores within the membrane of the living cell through which the biologically active molecule can traverse the cell membrane, but not lyse the living cell.

In accordance with another aspect of the present disclosure there is provided a device capable of inserting a biologically active molecule into a living cell including a fluid channel including a fluid channel including at least two fluid inputs and a fluid output configured to allow a fluid flow including two or more laminar sheath fluid streams of living cells and biologically active molecules through the channel; and a first electrode and a second electrode on opposite sides of the fluid channel to which electrical potentials can be applied to form an electric field directed across the fluid channel, wherein the dimensions of the fluid channel and the two or more laminar sheath fluid streams are sufficient to force the cells to pass through the space between the electrodes in a single layer so a living cell in the fluid flow is maintained in a similar position as other living cells in the fluid flow as they pass through the electric field between the first and second electrodes in a manner that prevents one living cell from shielding another living cell from the applied electric field, wherein the strength of the electric field to which the living cell is exposed is sufficient to form pores within the membrane of the living cell through which the biologically active molecule can traverse the cell membrane, but not lyse the living cell.

In accordance with another aspect of the present disclosure there is provided a method for inserting a biologically active molecule into a living cell including flowing fluid including living cells and biologically active molecules through a channel between two electrodes capable of generating an electric current, each electrode disposed on opposite sides of the channel; passing the cells through a space between the two electrodes in a single layer so a living cell in the fluid flow is maintained in a similar position as other living cells in the fluid flow as they pass between the two electrodes; and applying an electric voltage across the two electrodes while the living cell is passing between the two electrodes in a manner that prevents one living cell from shielding another living cell from the applied electric field, wherein the strength of the electric field to which the living cell is exposed is sufficient to form pores within the membrane of the living cell through which the biologically active molecule can traverse the cell membrane, but not lyse the living cell.

These and other aspects of the present disclosure will become apparent upon a review of the following detailed description and the claims appended thereto.

DETAILED DESCRIPTION

Figure 1:
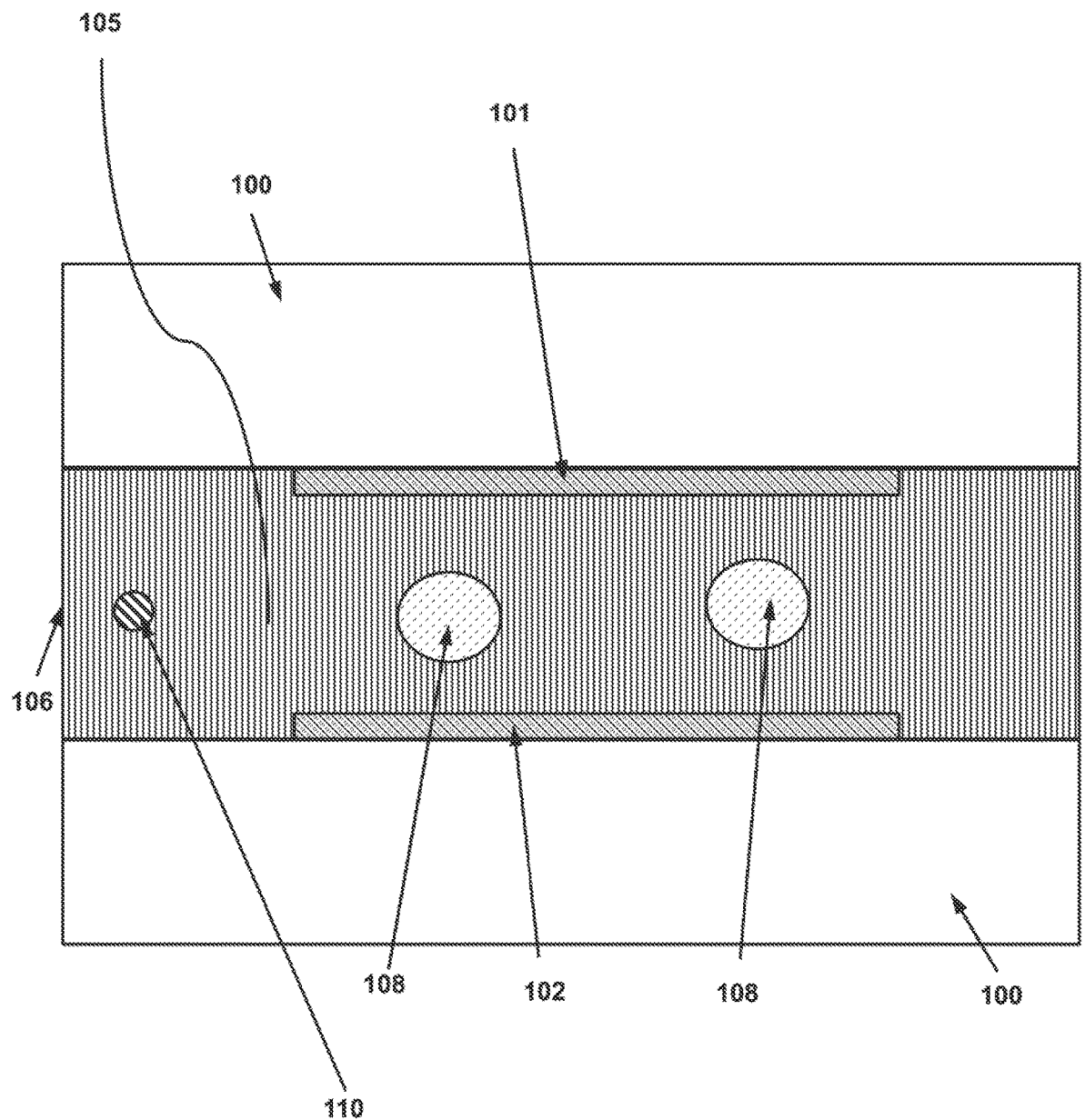
FIG. 1 is a cross sectional schematic view of a portion of a fluid channel device in accordance with an embodiment of the present disclosure.

The present disclosure relates to a system, method and device for the introduction of a biologically active molecule into a living cell by electroporation. The disclosure allows for monitoring and controlling cell location, motion, and exposure to electric fields between electrode pairs within the device such that each cell is exposed to similar electrical and chemical conditions during electroporation. In an embodiment, an electroporation device contains a fluid channel flanked by two electrodes on opposite sides of the channel to which electrical potentials can be applied to create an electric field across the channel between the electrode pair. The dimensions of the fluid channel combined with the characteristics of the fluid flow provide sufficient control to maintain the individual living cells within the fluid flow at similar positions with respect to proximity to the passing electrode pair. As the living cells flow through the channel between the electrodes the distance from the cell to each electrode is held to be nearly constant and in a manner that prevents one living cell from shielding another living cell from the applied electric field. Typically, the cell flow is one layer thick in the channel dimension between the opposing electrode pairs so that the cells are independently exposed to the same electrical current formed in the channel when passing between the electrode pairs. The channel has no restriction on distance in the other two dimensions of channel length and opposing channel walls not flanked by the electrodes. The cells flow through the channel at a set flux, and these features enable the user to apply precise electric fields to the cell. The strength of the electric field is strong enough to form pores within the membrane of the living cell through which biologically molecules can traverse the cell membrane, but weak enough to not lyse the cell.

The device includes one or more fluid inputs and at least one fluid output. When the device includes a single fluid input a single laminar fluid stream is created. The single fluid stream contains living cells in combination with biologically active molecules for introduction of the biologically active molecule into the living cell by electroporation. Suitable spacing between the electrodes includes about 2 to 5 times larger than the diameter of the cell, or smaller than approximately two times the typical cell diameter, forcing the cells to pass through the space between the electrodes in a single layer. The living cells in the single fluid flow are maintained in a similar position as other living cells as they pass through the electric field between the electrode pairs so each cell is exposed to similar electrical and chemical conditions during electroporation. Suitable distance between the electrodes of an electrode pair includes a range of from about 50 micrometers to about 100 micrometers, or less than about 100 micrometers.

When the device includes at least two fluid inputs multiple laminar sheath fluid streams are created. Each fluid input can accept a separate fluid stream. For example, one stream contains living cells and another contains the biologically active molecules. Thus, the living cells and the biologically active molecules flow through separate fluid inputs into the channel. The streams are separated by laminar sheath flow. The dimensions of the fluid channel are constructed to accommodate the laminar flow separated streams so that living cells contained in the fluid flow are maintained in a similar position as other living cells as they pass through the electric field between the electrode pairs. In a system with multiple sheath flows, the sheath flows separate the cells from the electrode and channel walls with a constant spacing controlled by the flow rates. The multiple sheath flow devices allow the chemical composition of the fluid on opposite sides of the cell to differ permitting an efficient electrical drive of charged molecules such as DNA and RNA into the cells. The flow of liquid through the channels can be unvarying in time, which simplifies the process and assures that all cells experience the same combination of conditions during electroporation as they pass through the flow channel. Suitable distance between the boundaries of the sheath flow containing the living cells between paired electrodes includes from about 50 micrometers to about 100 micrometers; less than about 100 micrometers; about 2 to 5 times larger than the diameter of the cell; or smaller than approximately two times the typical cell diameter, forcing the cells to pass through the space between the electrodes in a single layer. The device can contain one or more fluid outputs. In this embodiment, the distance between the electrode pairs can be greater than that noted above since the living cells in the sheath stream are maintained in a similar position as other living cells as they pass through the electric field between the electrode pairs by the adjacent sheath flows. A suitable distance between the electrodes of an electrode pair includes from about 50 micrometers to about 500 micrometers. Another advantage of an embodiment of the disclosure is that the user can manipulate the chemical and electrical properties of the environment at different positions along the length of the channel. Furthermore, an embodiment of the disclosure allows the user to monitor various properties of the cells and/or the solution in order to modify and optimize the flow and voltage parameters in real time.

Channel

FIG. 1 shows a cross-sectional schematic view of an embodiment of the device. A flow channel 106 lies between two chips 100. A positive electrode 101 lies on an inner flow channel surface of upper chip 100 opposite a negative electrode 102 which lies on an inner flow channel surface of lower chip 100. A liquid stream 106 of buffer containing cells 108 and nucleic acids or other biological molecules 110 to be electroporated flows between lower chip 100 and upper chip 100.

By limiting the gap dimension between electrodes to be about 2 to 5 times larger than the diameter of the cell or less than approximately two times the cell diameter, there is not enough physical space for more than one cell in the flowing stream to be located in the channel gap between the electrodes. This controlled gap spacing as well as operating in the laminar flow regime (no turbulent flow) allows for controlled positioning of a single given cell between the electrodes in this one plane. While the flow channel is narrow in proximity to the electrodes, the channel can be made as wide as necessary in the orthogonal dimension to achieve the desired flow rate of the cells through the channel. Similarly, the length of the channel has no restrictions. Control of the distance between the electrodes allows each cell to be isolated or held in a similar position relative to the electrodes. Thus, each cell is essentially subjected to a similar electrical and chemical environment while, at the same time, high total cell throughput is possible. In one embodiment of the device, the channels can be manufactured so that distance between the chips 100, and thus the electrodes 101 and 102, can be adjusted to accommodate different types and sizes of living cells. The chips 100 on which the electrodes 101 and 102 are mounted can be made of any nonconductive or electrically insulating material, such as glass, plastic or optically transparent material.

Figure 2:
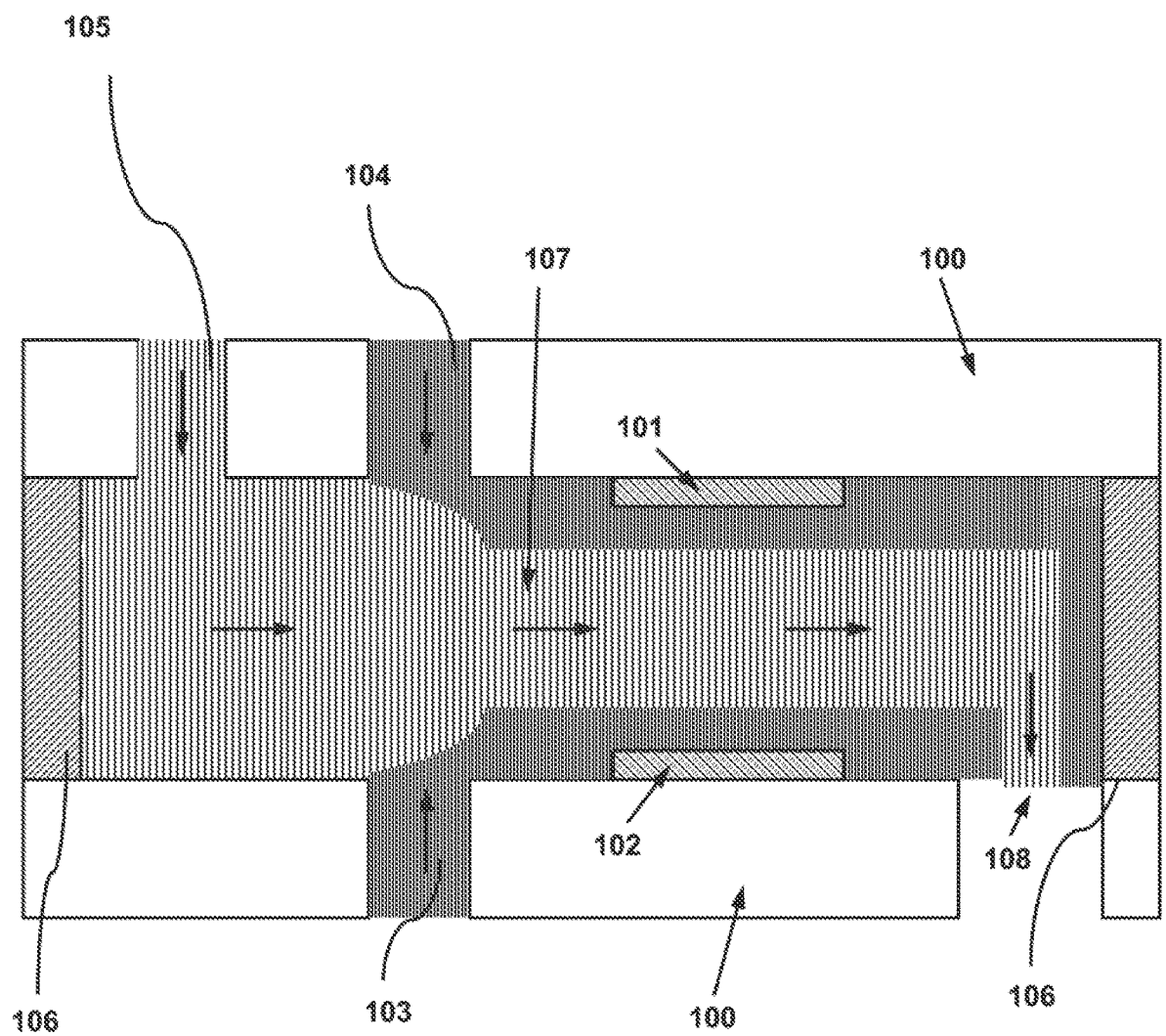
FIG. 2 is a cross sectional schematic view of a fluid channel device including a fluid channel system, multiplicity of fluid inputs, output, and a pair of electrodes.

FIG. 2 shows a cross-sectional schematic view of an embodiment of the device. A flow channel 107 lies between chips 100 with patterned electrodes; a positive electrode 101 lies opposite a negative electrode 102. FIG. A lower liquid stream 103 of a high conductivity buffer containing nucleic acids or other biological molecules to be electroporated flows adjacent the negative electrode 102. An upper liquid stream 104 of a high conductivity buffer flows adjacent the positive electrode 101. A middle liquid stream 105 of a low conductivity buffer containing cells 108 to be electroporated flows between lower liquid stream 103 and upper liquid stream 104. The upper liquid stream 104, middle liquid stream 105, and lower liquid stream 102 are separated by laminar flow.

Figure 4:
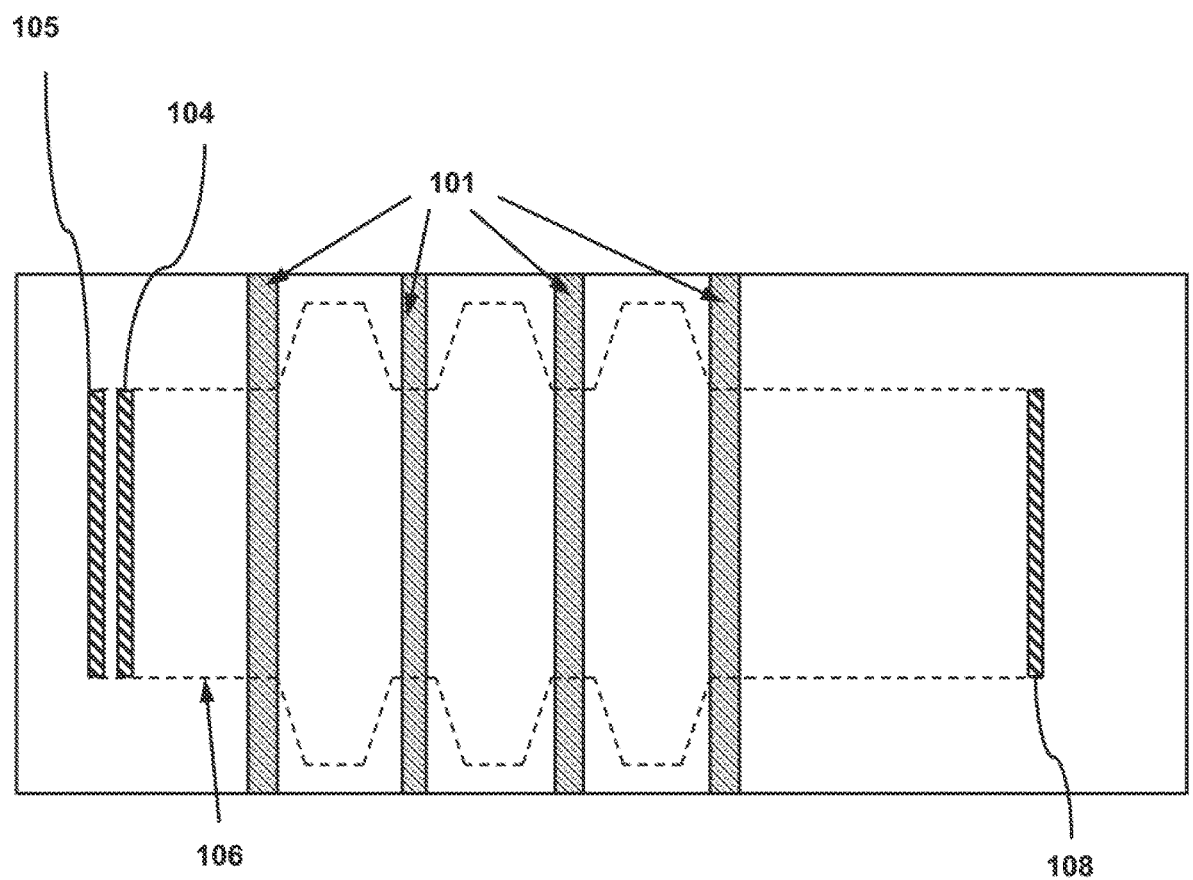
FIG. 4 shows a plan view schematic of a flow channel device with variable width in a direction orthogonal to the direction of flow.

In FIG. 2, fluid from the inputs 103, 104, and 105 flow through the channel 107 and exit the device via an output 108 flow. Spacers 106 are used to change direction of the flow. The flow channel can be made in various geometries and have either a constant or variable width. For example, FIG. 4 illustrates a top view of a device having a variable width channel, wherein the channel is narrower as it passes by the electrodes 101, and wider in between electrodes. Each upper electrode 101 is paired with a lower electrode 102 (not shown). Thus, spacer outline 106 illustrates an area of fast flow across the electrodes 101 and an area of slow flow in between the electrodes 101. The stream from an upper liquid outlet 104 and the stream from a middle liquid outlet 105 are separated by laminar flow and exit via outlet 108.

Figure 6:
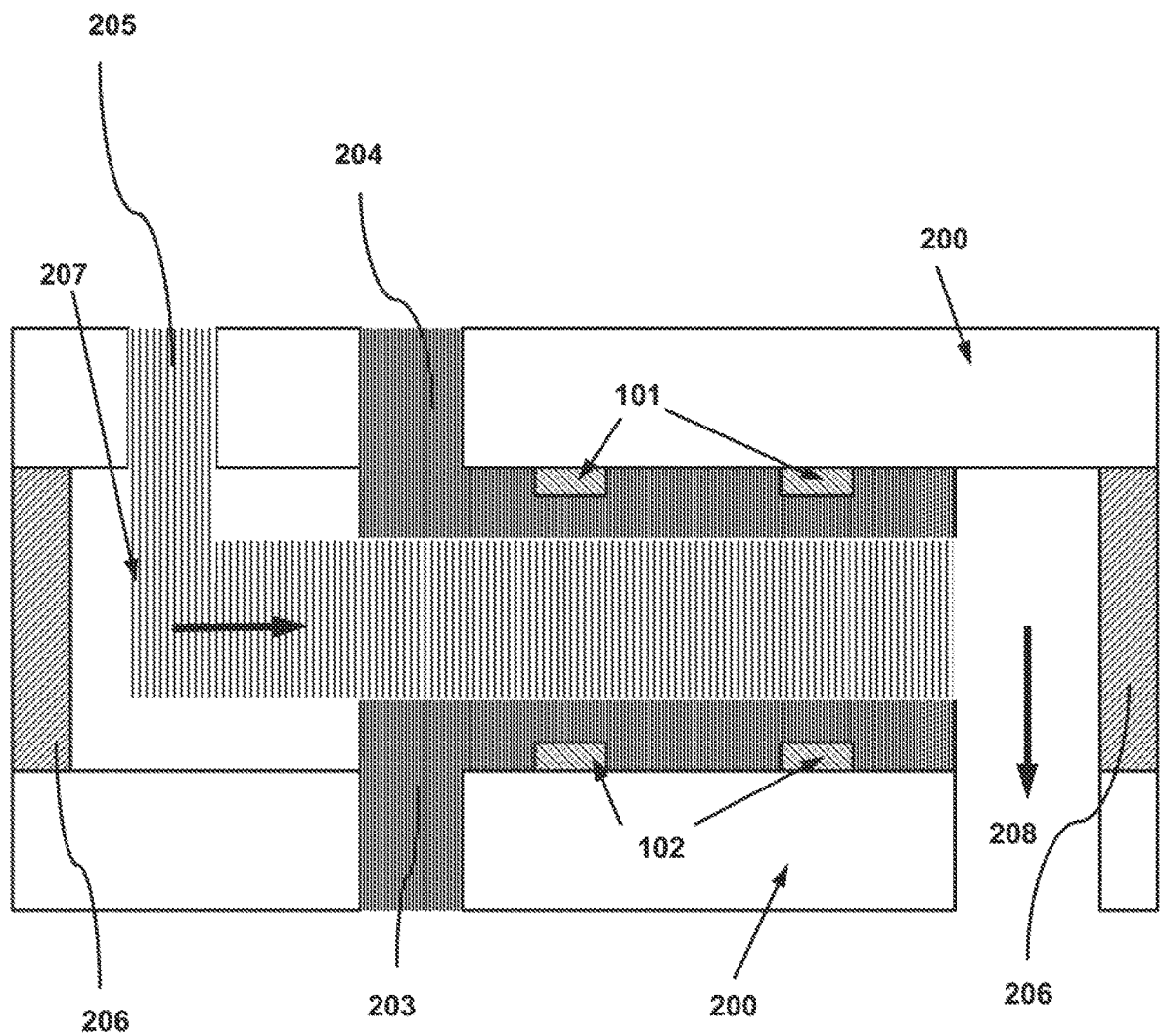
FIG. 6 shows a cross-sectional schematic view of an embodiment of the device.

FIG. 6 shows a cross-sectional schematic view of an embodiment of the device. The flow channel 207 lies between chips 200 with patterned paired electrodes; two positive electrodes 101 lie opposite two negative electrodes 102. The distance between the two electrodes is selected to be slightly larger than the diameter of the living cells flowing in fluid input 205. While the flow channel is narrow in proximity to the electrodes, the channel can be made as wide as necessary in the orthogonal dimension to achieve the desired flow rate of the cells through the channel. Similarly, the length of the channel has no restrictions. Control of the distance between the paired electrodes allows each cell to be isolated or held in a similar position relative to the paired electrodes, taking into account the laminar flow established by fluid inputs 203, 204, and 205. Thus, each cell is essentially subjected to a similar electrical and chemical environment while, at the same time, high total cell throughput is possible. Fluid from the inputs 203, 204, and 205 flow through the channel 207 and exits the device via an outlet flow 208. Spacers 206 are used to change direction of the flow.

Figure 7:
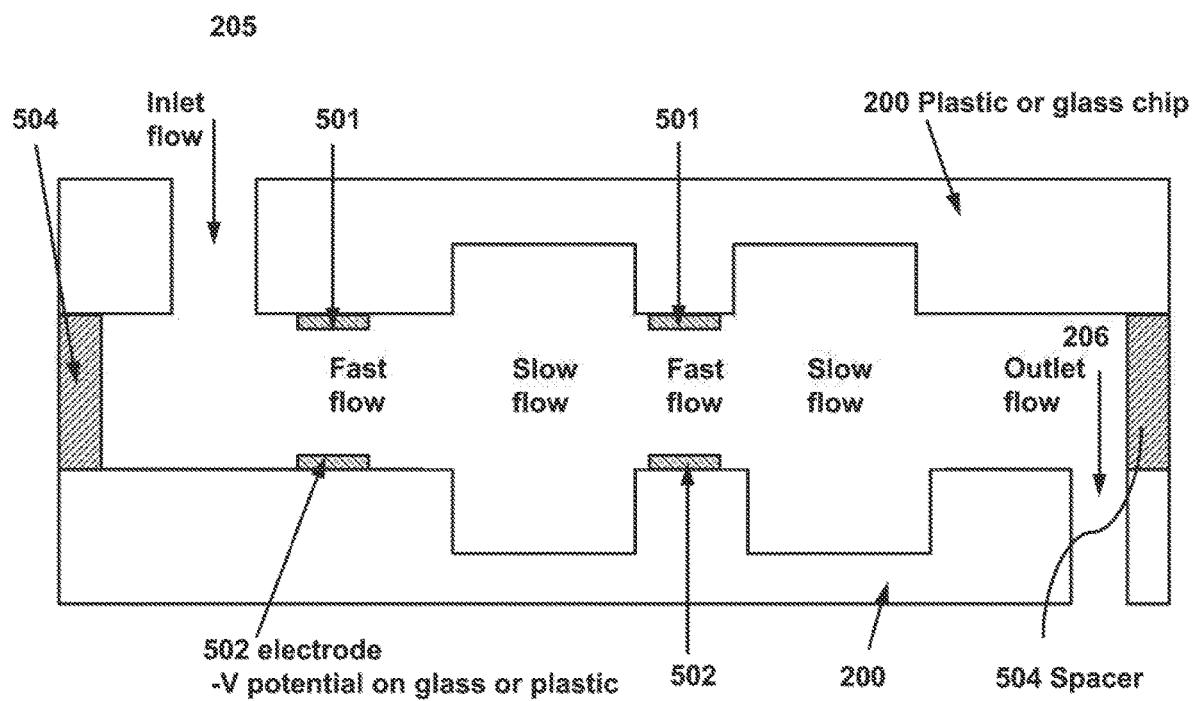
FIG. 7 shows a side view of a device having a variable height channel in chip.

The flow channel can be made in various geometries and have either a constant or variable height. For example, FIG. 7 illustrates a side view of a device having a variable height channel between chips 200, wherein the channel is lower as it passes by the paired electrodes 501, 502, and taller in between the paired electrodes 501, 502. Thus, the channel illustrates an area of fast flow across the electrode pairs and an area of slow flow in between the electrode pairs. The stream from an upper liquid inlet 205 and lower liquid outlet 206 changes flow direction by spacers 504.

Fluid Inputs and Streams

The fluid can flow through the channel at a rate of 0.1 cm/s, with a relevant range of flow rate between 0.001 cm/s and 10 cm/s. The volume of fluid flowing through the channel relates to the cross sectional area of the flow channel. For example, for a channel 2 cm wide and 100 micrometer high the volumetric flow rates would be in the range of from about 0.2 microliters/s to 2 milliliters/s.

The device permits the use of multiple inputs of fluid through slits in the channel device to provide flow with different layers of solution composition. The flow rate of two or more fluid streams into the channel can be controlled to create a sheath flow. In one embodiment of the device, the channel 107 (FIG. 2) delivers a low conductivity buffer containing living cells to be electroporated through a liquid sheath. An optional channel 104, on the same side of the device as channel 105, delivers a high conductivity buffer. Another channel 103, located on the opposite side of the device, also delivers high conductivity buffer; in FIG. 2 this buffer contains the biologically active molecules that are to be inserted into the living cells. Various streams of cells or molecules enter the channel via these inputs, and these streams can have the same or different flow rates. If desired, streams with different flow rates adopt laminar flow through the channel. Thus, the streams flow in parallel through the channel and remain largely separated, mixing slowly only through diffusion. In this manner, individual cells in the stream of living cells can be isolated between the electrode pair by the laminar flow of the adjacent fluid streams.

The use of multiple inputs of fluid can prevent various types of fouling or contamination. For example, the molecules or nucleic acids to be inserted into the cells can exist in a separate solution from the cells. This can be useful because certain molecules, like RNA, may not be stable in the vicinity of living cells due to enzymes on the cell surface or cell culture media. Also, it is known that degradation of the electrodes can result in the release of contaminants that are toxic to cells. The separate fluid layers ensure that the cells remain free from contaminants from the electrodes. Further, the cells themselves are kept out of contact with both the surface of the chip and the electrodes preventing possible contamination.

Alternatively, an embodiment of the device can contain a single fluid input through which a homogenous solution of cells and biologically active molecules enters the channel. The stream consists of a conductive buffer solution containing the biologically active molecules that are to be inserted into the living cells. The biologically active molecules are chosen from among the categories of nucleic acids, drug molecules, and other biologically active molecules. Compared to the device having multiple inputs, this might be advantageous in that there is a greater opportunity for the cells and the biologically active molecules to come into contact with one another and could increase the efficiency of transformation.

In one embodiment, the inputs 104, 105 introduce fluid streams to the channel so that the streams turn at an angle before flowing in between the electrodes. In FIG. 2, this angle is shown as 90° but the angle can be any angle including 0°. In this case, spacer 106 helps to direct the flow from the inlets 104, 105.

Similarly, in one embodiment of the disclosure, the flow turns a corner before exiting the device through the output 108. In FIG. 2, this angle is 90°, but this angle can be any angle, including 0°. In this case, spacer 106 helps to direct the flow to the outlet.

Fluid streams interface to the device via interconnects, a manifold, or discreet fluid path connections. The manifold serves to reformat the tubing or conduits into the receiving slit-port of the device (103, 104, or 105 in FIG. 2). The manifold may have surface area changes for this purpose. The manifold may have features to enhance mixing or maintain laminar flow characteristics.

The manifold may be machined, molded, casted, or the like. The manifold may also be fabricated as part of the device or bonded to the device via a permanent or non-permanent bond. Sealing between the manifold and the device may be hermetic, compression-based, O-ring-based, gasket-based, adhesion-based, fused, luer locked, flat bottom compression-based, tapered ferrule-based, frusto-conical compression-based, or the like.

Cells and the bioactive materials may be presented to the device via several approaches. They may be injected via a robotic fluid handling platform or injection system or connected via biocompatible containers. Bioprocess containers include polymer bags, T-flasks, conical tubes, media bottles, well plates, or the like. These vessels may be one time use or reusable when proper sterilization is performed. Connections to the fluid delivery path may be achieved by compression seals, threaded connections, clamping compression, luer lock mechanisms, O-ring seals, friction seals, gaskets seals, clamping, or similar connections. In the case of pneumatic displacement, the container itself may be pressurized or be contained inside a pressurized vessel.

In another embodiment, the cells may be presented to the device by custom cartridges that interface to the pumping or fluid manipulation system.

Fluid Output

The fluid outlet 108 is shown in FIG. 2. After electroporation, a mixture of all of the fluid streams can leave the device via this outlet. The solution may be transferred to sterile polymer bags, T-flasks, conical tubes, media bottles, well plates, or the like and allowed to recover at 37° C. The cells may then be re-suspended in standard tissue culture medium and plated for immediate use in cellular assays, cryopreserved for future use, or used as desired.

Electrodes

The separation between electrodes in accordance with the present device is small therefore requiring an applied voltage of only a few volts to perform the electroporation. This is in contrast to the need for voltages up to several thousand volts that are normally required for prior art electroporation. For example, it is known in the literature that a transmembrane electric field of less than 1 kV/cm is required to porate the cell membrane (Weaver and Chizmadzhev, 1996). However, for a distance between the electrode pairs of 100 micrometers, this requires approximately a 5 V potential difference to porate an average mammalian cell in accordance with the present device. Suitable voltage differences across a living mammalian cell include the following range: 0.1 V to 10 V. For example, for a distance between the electrodes of 100 micrometers this range corresponds to an electric field of 10 V/cm to 1000 V/cm.

The flow channel can have one or several electrically independent electrode pairs. For example, in FIG. 4, four sets of electrode pairs 101 are shown. Connections to the electrodes are made by using clips or conduction adhesive to connect these to a variable-voltage power supply or batteries with a voltage divider. An ammeter can be used to monitor the current flowing between electrodes for monitoring and controlling the process.

The electrodes can apply either a constant or pulsating voltage through the channel. If a pulsating voltage is desired, pulse duration of from about 0.01 millisec to about 100 millisec is suitable. The plurality of electrode pairs can be patterned to create spatially varying electric fields. The electrodes may be patterned by the use of a photomask in the photolithographic process or by a shadow mask in the sputtering or deposition process. Patterning allows for the fabrication of electrodes with varying geometric shape.

Manufacturing the Device

Figure 3:
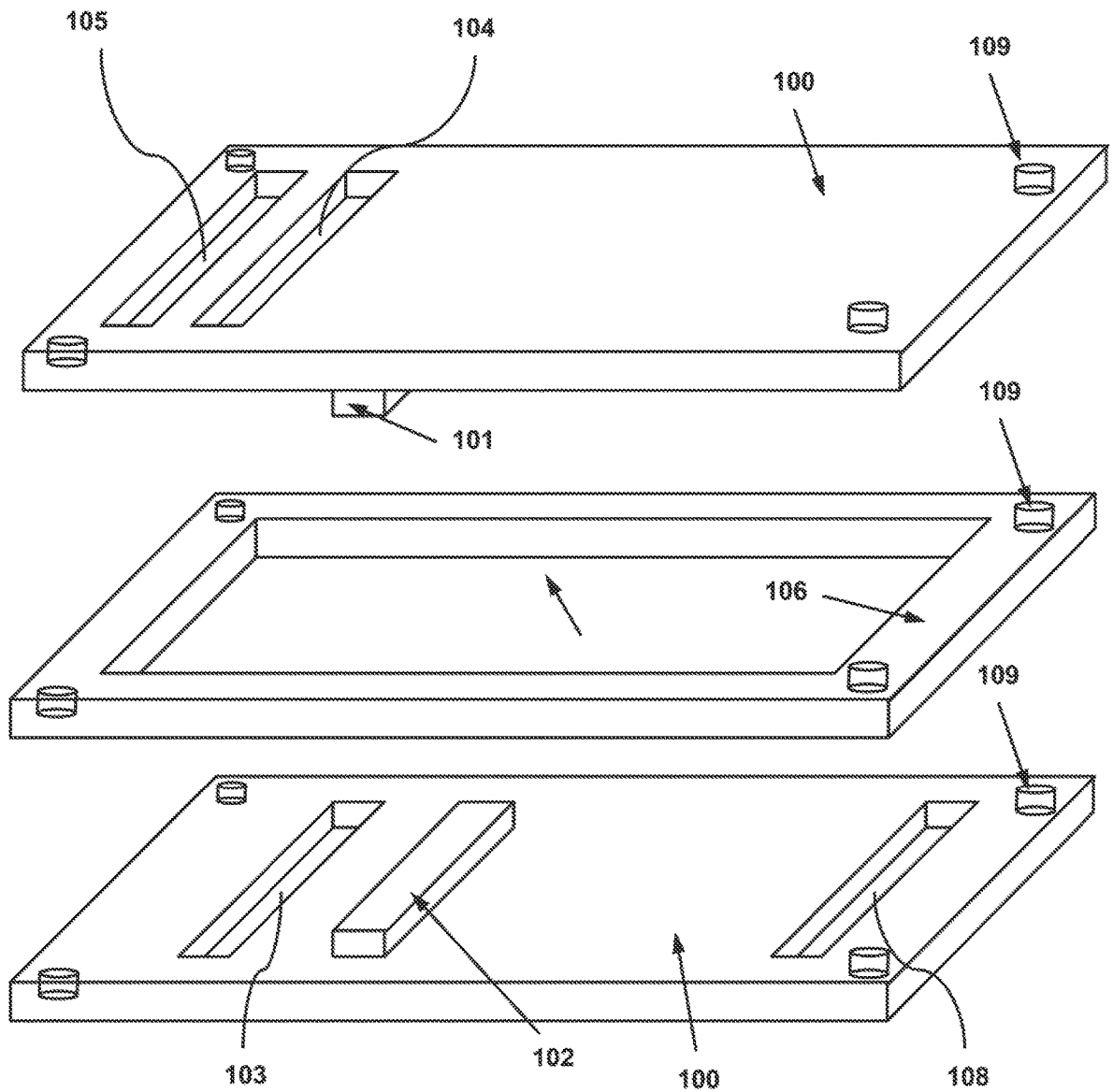
FIG. 3 shows an embodiment of a device constructed with three layers.

One embodiment of the device is constructed from a three-layer stack of polymer substrates or plastics as shown in FIG. 3. All three layers are laser cut with a small beam spot, high resolution $CO_2$ laser. The layers on which the electrodes are fixed are cut from 1 mm thick acrylic slabs, creating opposite surfaces of the channel. A middle layer 106 defines the distance between the electrode pairs 101, 102. In the embodiment shown in FIG. 3, the three dimensions of the layers are the same. Although it is most practical for the layers to be the same in dimensions in the plane that the stream flows, these dimensions can be different from one another. One way to manufacture these layers is to use a laser to cut acrylic pieces to microscope format 25×75 mm, add fluid inlet slits or ports 103, 104, 105 to chips 100, respectively and add alignment holes 109 to facilitate assembly. A thin film electrode (50 nm) of a gold-palladium (Au/Pd) mixture is deposited by physical vapor deposition on the inside surface of each acrylic piece. The 100-micron thick middle layer 106 polymer film with medical adhesive on each side is cut to shape and also receives the corresponding alignment holes via the laser cutting process. After laser cutting, the three pieces are placed on a jig containing alignment pins corresponding to the alignment holes in each layer. The sandwich assembly is then compression-bonded in a press. This two-step process of laser cutting and compression assembly is amenable to mass production and allows for a cost-effective consumable to be created. The process can be used to manufacture hundreds of thousands of devices per year. This is in contrast to many other types of prior art non-electroporation microfluidic devices that typically require expensive capital equipment and a large number of chemical processing steps.

Alignment of the device layers may be conducted by optical positioning or a physical means such as datum pads, alignment pins, or structures. The device layers may have receiving features for use with a jig alignment piece or system. Alternatively, the alignment features may reside in the device layers as so no jig or peripheral alignment system is necessary. These may include pin-like structures or features that snap together.

The flow cell could also be produced by an injection molding process, where the volume can scale to millions of single-use devices per year, using one injection molding press with a multi-cavity mold.

This disclosure allows for architectures for manufacturing the device that are readily amenable to injection molding. In this device, all the layers may be formed via injection molding. The fluidic channel may be formed in one layer at full depth or, alternatively, the channel may span two or more layers, where the full depth is achieved upon assembly. Injection ports may be created via core pins. Alternatively, the fluid inlets may be added post molding as a secondary operation or structure. The layers may be molded from the planar surface or from the edges. Appropriate and efficient part release from the mold cavity is known in the art.

The molded layers may be assembled together through mechanical connection, adhesion, bonding, welding (including ultrasonic and laser), fusing, melting, or the like. Additionally, there may be another material between the layers for connection and sealing such as, but not limited to, a gasket, O-ring, washer, or the like. Alternatively, sealing can be achieved through press tight or bonding features.

In another embodiment, the fluid channel may reside in one layer and the opposing sealing structure is a non-injected molded part such as a film, tape, or planar material containing necessary fluid inlets.

In another embodiment, the device may be created by three-dimensional printing or additive manufacturing processes. Other fabrication techniques include compression molding, casting, and embossing.

In another embodiment, devices are made from glass via lithography and wet or dry etching. Alternatively, the devices may be physically machine via computer numeric control (CNC) or ultrasonic machining.

In other embodiments, the devices can be made from various materials, such as, for example, where at least one layer is glass, where at least one layer is plastic, where one of the layers is optically transparent, or where the channel material is electrically insulating.

Manufacturing the Electrodes

The formation of patterned electrodes on the flow channel surface can be accomplished with a variety of readily available techniques. One method is to use the process of sputtering for deposition of a conducting metallic conducting layer such as gold, platinum, aluminum, palladium, other metals, or alloys of multiple metals. Gold-palladium is an example of a metallic alloy that can be used to compose the electrodes. The electrodes can be made of an optically transparent material to allow observation of the motion of the living cells in the fluid channel of the device. To generate transparent conducting layers, films of indium-tin oxide (ITO) are frequently used. After metal deposition, these conducting layers can be patterned by masking and etching to remove material where it is not wanted in order to form the desired patterned electrode shapes. Appropriate masks may be formed from photoresist using common photolithographic exposure processes.

Another method for forming electrodes is to deposit electrically conducing films made of metals or other conducting layers such as ITO. By depositing them through a prepositioned mask, sometimes called a shadow mask, the films are positioned in proximity to the surface to be coated so that the conducting layer reaches the surface only where previously opened regions have been formed in the mask. In addition, a related technique called "lift-off" can be used, in which a patterned photoresist layer can be used to shape the pattern of deposited conducing material.

The deposition of layers of conducing ink can be performed by brushing or spraying, followed by heating to form patterned conducting films.

These thin film patterning processes are well known to those skilled in the art. In this case, the thickness of the films is desired to be in the range of from 5 nm to 5 micrometers, with a preferred range of from 10 nm to 100 nm.

In one embodiment of the device, electrodes can be formed by inlaying wires in grooves formed in the chip (100 in FIG. 1) instead of affixing the electrodes to the chips. In this embodiment, grooves are machined into the chip, for example a plastic chip, and the electrodes are metal. Preferably, the electrodes are gold or a gold-plated metal. The wire is then glued into the groove.

An embodiment of a system includes an electroporation device, fluid delivery system including a pump, temperature control and optical and electrical monitor of the cells to obtain real-time feedback on the cell modification process. Feedback can be obtained by monitoring the electrical current passing between the two electrodes to provide information about living cell modifications, imaging of the living cells to provide information about living cell modifications or monitoring fluorescence of the living cells to provide information about living cell modifications.

An embodiment includes a system for inserting a biologically active molecule into a living cell includes an electroporation device capable of performing a cell modification process including inserting a biologically active molecule into a living cell contained in a fluid flow by flowing fluid including living cells and biologically active molecules through a channel between two electrodes, each electrode disposed on opposite sides of the channel; passing the cells through a space between the two electrodes in a single layer so a living cell in the fluid flow is maintained in a similar position as other living cells in the fluid flow as they pass between the two electrodes; and applying an electric voltage across the two electrodes while the living cell is passing between the two electrodes in a manner that prevents one living cell from shielding another living cell from the applied electric field, wherein the strength of the electric field to which the living cell is exposed is sufficient to form pores within the membrane of the living cell through which the biologically active molecule can traverse the cell membrane, but not lyse the living cell; a fluid delivery system including a fluid source and a fluid pump in fluid communication with the electroporation device, an electrical current source in electrical communication with the pair of electrodes; a temperature control in thermal communication with in the fluid flow; and an optical and electrical monitor of the living cell capable of obtaining real-time feedback on the cell modification process.

Figure 5:
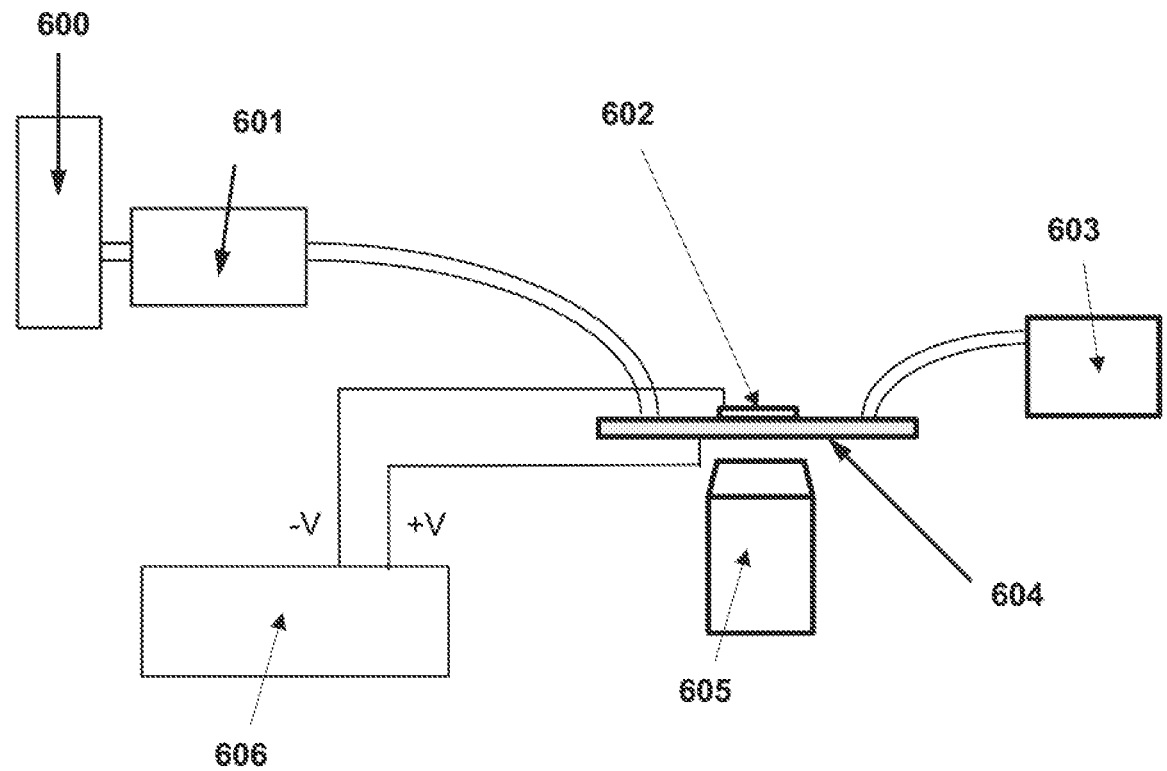
FIG. 5 shows a schematic of a system for control of fluid flow and electrical voltage and optically and electrically monitoring controlled electroporation.

One advantage to the electroporation device over the prior art is the ability to optically and electrically monitor the cells to obtain real-time feedback on the cell modification process. FIG. 5 illustrates one embodiment of the device; this is a microfluidic electroporation system with an observation microscope 605. Accordingly, the fluid flow controller 601 or voltage controller 606 can be adjusted as required to optimize the process efficiency and cell viability. In this embodiment, the microscope is positioned so that it views a reservoir 602 that contains biologically active material. For example, this could be nucleic acids. The fluid from input cell reservoir 600 flows through the channel of the microfluidic electroporation chip 604 and across the field of view of the microscope 605, and into a cell collection reservoir 603, thus enabling the user make adjustments as necessary to improve the efficiency of transformation.

Temperature control of the solutions or materials in contact with the fluids may be implemented at any instance(s) in the system, including heating and cooling. This may include static control or temperature cycling.

The device can be interfaced to a fluid delivery system. A fluid delivery apparatus or pump operating with flow controller 601 is configured to displace, preferably, indirectly displace, the fluid from the input cell reservoir 600 to establish a fluid flow within the fluid path. The fluid displacement apparatus is capable of providing positive and/or negative displacement of the fluid. The delivery pump includes mechanisms based on peristalsis, pneumatics (pressure displacement), hydraulics, pistons, vacuum, centrifugal force, manual or mechanic pressure from a syringe, and the like. Preferably, the fluid is indirectly displaced by the pump without the fluid directly contacting any of the moving parts of the apparatus, such as, for example, a peristaltic pump acting upon a fluid filled tube. Alternatively, a pneumatic displacement mechanism may be used where a head pressure displaces liquid from a pressurized vessel. Conversely, fluid may be directly displaced by an apparatus, when the fluid is displaced by directly contacting any of the moving parts of the apparatus, such as, for example, the plunger of a syringe pump.

The pump may include a flow sensor for monitoring the flow rate or the flow sensor may provide closed loop feedback to the pump control system. The closed loop feedback can ensure accuracy and reduce pulsing. The pump displaces fluid contained in flexible tubing to create a fluid stream. The system may operate with an inline flow sensor configured to directly measure the fluid flow rate as the fluid passes the sensor. The system includes a feedback control in communication with the fluid displacement apparatus and the inline flow sensor. The inline flow sensor measures the flow and communicates with a feedback control mechanism. Suitable types of flow sensor mechanisms include thermal pulse, ultrasonic wave, acoustic wave, mechanical, and the like. The inline sensor may be mechanical-based, electrically-based, motion-based, or microelectromechanical systems (MEMS)-based. The sensor mechanism may be thermal, ultrasonic or acoustic, electromagnetic, or differential pressure. One example of a sensor suitable for use in accordance with the present disclosure is a thermal-type flow sensor where the sensor typically has a substrate that includes a heating element and a proximate heat-receiving element or two. When two sensing elements are used, they are preferably positioned at upstream and downstream sides of the heating element relative to the direction of the fluid (liquid or gas) flow to be measured. When fluid flows along the substrate, it is heated by the heating element at the upstream side and the heat is then transferred non-symmetrically to the heat-receiving elements on either side of the heating element. Because the level of non-symmetry depends on the rate of fluid flow and that non-symmetry can be sensed electronically, such a flow sensor can be used to determine the rate and the cumulative amount of the fluid flow. This mechanism allows the flow to be measured in either direction. In one preferred embodiment, the temperature sensors and the heating element are in thermal contact with the exterior of the fluid transporting tube and as the fluid stream only contacts the internal surfaces of the tube, the fluid media avoids direct contact with the sensor and heating elements. This format type allows highly accurate and highly sensitive flow measurements to be performed.

EXAMPLES

The disclosure will be further illustrated with reference to the following specific examples. These examples are given by way of illustration and are not meant to limit the disclosure or the claims to follow.

Example 1—Electroporation of Mammalian Cells with a DNA Plasmid

This example describes an embodiment where the flow electroporation device is used to electroporate mammalian cells with a DNA plasmid. Chinese hamster ovary (CHO-K1) cells (ATCC) are electroporated with a plasmid that expresses green fluorescent protein using the flow-through electroporation device described. Cell viability can be determined based on the uptake of propidium iodide. The electroporation efficiency can be determined using fluorescent observation of the number of cells that express the green fluorescent protein relative to the total number of cells.

The cells are cultured in an incubator at 37° C. and 5% $CO_2$. The cells can be cultured in a synthetic medium, such as Dulbecco's modified Eagle's Minimum Essential Medium (DMEM, Sigma, St. Louis, MO) supplemented with 10% fetal bovine serum (Sigma) and 100 mg/mL streptomycin (Sigma). When the cell suspension density reaches a certain value, for example, $2 \times 10^6$ cells/mL, the cell suspension is diluted with additional culture medium. Prior to introduction into the device, a 10 mL sample of the suspension is centrifuged at 300 g for 5 min. The supernatant is discarded and the cells are re-suspended in a low conductivity buffer (described below). The cell suspension density for electroporation is preferably $1 \times 10^8$ cells/mL with a range between $1 \times 10^7$ and $1 \times 10^9$ cells/mL.

The low conductivity buffer is composed of 0.8 mM $Na_2HPO_4$, 0.2 mM $KH_2PO_4$, 0.1 mM $MgSO_4 \cdot 7H_2O$, and 250 mM sucrose, at a pH of 7.4. This buffer is made by dissolving 0.1136 g of $Na_2HPO_4$, 0.0272 g of $KH_2PO_4$, 0.02465 g of $MgSO_4 \cdot 7H_2O$, and 85.575 g of sucrose in 1 liter of water, and subsequent adjustment of the pH. The sucrose is used to equalize the osmotic pressure of the buffer with that of the cells. The buffer is filtered with a 0.2-micron membrane and stored at 4° C. The concentrations of salts in the buffer as described result in a solution with electrical conductivity of approximately 0.014 S/m. The preferable range of the electrical conductivity of this buffer is between $1 \times 10^3$ and 0.5 S/m.

The pAcGFP-C1 plasmid (4.7 Kb, Clontech, Mountain View, CA) encodes a green fluorescent protein (GFP) from

*Aequorea coerulescens* and contains an SV40 origin for replication in mammalian cells. The GFP protein is excited at 475 nm and emits at 505 nm. The plasmid is amplified in *E. coli* and purified using the QIAfilter Plasmid Mega Kit (Qiagen, Valencia, CA) according to the manufacturer's instructions. The plasmid DNA is dissolved in Tris-EDTA buffer and stored at −20° C. until use. The plasmid DNA concentration is determined by ultraviolet (UV) absorbance at 260 nm. Prior to an electroporation experiment, the plasmid is precipitated with ethanol and resuspended in phosphate buffered saline (PBS, 137 mM NaCl, 2.7 mM KCl, 10 mM $Na_2HPO_4$, 1.8 mM $KH_2PO_4$) buffer with an electrical conductivity of approximately 1.5 S/m at a concentration of approximately 40 ug/mL. The range of the electrical conductivity of this buffer is between $1\times10^2$ and 10 S/m. The range of the plasmid concentration is between 0.01 and 100 ug/mL.

The low electrical conductivity buffer used for the cell flow inlet 105 (FIG. 2) used in combination with a higher electrical conductivity buffer (PBS) for the upper and lower sheath inlets 103 and 104 flow layers (FIG. 2) results in an electric field that is substantially larger across the cell flow layer for a given applied voltage. For a typical experiment, the pressure of each flow is adjusted so that the cell flow layer is approximately 50 microns deep and the upper and lower sheath flow layers are approximately 25 microns each in depth. The electrical conductivities of the low and high conductivity buffer are 0.014 S/m and 1.5 S/m, respectively. The electrical resistance of the sheath layer (for a voltage applied between the two chip surfaces 100 as shown in FIG. 2) is approximately 99% of the total resistance. This means that if 5 V is applied between the electrodes on the two chip plates that the electric fields in the streams adjacent to the electrodes is approximately 9 V/cm while the stream sandwiched between those two streams is 991 V/cm.

It is known that a difference of approximately 1 V between the interior and exterior of a cell will result in the formation of pores that can allow for the passage of nucleic acid molecules. The potential difference U across a cell membrane at a point on the surface of a cell in an external electric field of strength E is given by $U=fER \cos\theta$, where R is the cell radius, $\theta$ is the angle between the electric field and the normal to the cell surface, and f is a geometric factor that is typically around 3/2. This implies that to form pores at the poles of the cell the electric field should be about 1 kV/cm for a cell with radius of 8 microns.

With this electroporation device, the application of a 5 V potential difference between the top and bottom plates results in an electric field within the cell flow layer of about 1 kV/cm given the electric field strengths and flow layer depths described. The preferable range of applied voltages is between 1 V and 100 V. If the patterned electrodes are 2.5 cm by 0.5 cm in size, then for a 5 V applied potential, a current of about 0.17 A is generated and a power of 0.87 J/s is dissipated. This amount of power would increase the temperature of pure water in a device with dimensions 5 cm by 2.5 cm by 0.01 cm by 1.7 degrees C./s, assuming that no heat is dissipated through the boundary. The source for the applied voltage can be from a battery with a fixed voltage or a battery used in conjunction with a resistive voltage divider to enable the voltage to be varied over the selected range. Commercial voltage supplies are also readily available to provide selected voltages in the range of 1 V to 100 V. An alternative electrode size example includes electrodes with dimensions of 2.5 cm by 0.05 cm in size, then for a 5 V applied potential, a current of about 0.017 A is generated and a power of 0.087 J/s is dissipated. This amount of power would increase the temperature of pure water in a device with dimensions 5 cm by 2.5 cm by 0.01 cm by 0.17 degrees C./s. In a typical experiment, cells at a density of $1.0\times10^7$/mL are flowed through the chip at a volumetric rate of approximately 1.5 mL/min, with a preferable range between 0.01 and 100 mL/min. The nominal flow rate of 1.5 mL/min results in an average linear flow velocity of 1.0 cm/s. At this velocity, cells are subject to the electric field from an electrode that is 2.5 cm by 0.5 cm in width and length for 0.5 s. Assuming Hele-Shaw flow, the pressure difference across the input and output of the chip is about 40 atm. It is important to note that during the approximately 0.5 s that cells are subject to the electric field, that the plasmid DNA is electrophoretically driven toward the cell flow layer, assuming that the plasmid is in the lower sheath flow and that the top electrode is held at a higher voltage than the bottom electrode. Assuming a DNA mobility of $4\times10^4$ $cm^2/Vs$, the average time that it takes a DNA molecule to move half-way through a distance of 25 microns (the typical depth of the sheath flow layer containing the plasmid) is 0.34 s. A DNA molecule that reaches the cell flow layer is driven across it in about 10 ms.

Another important timescale is the cell sedimentation time for falling a distance of one-half of the cell flow layer thickness. Again assuming a cell radius of 8 microns, a difference in density between a cell and the surrounding fluid of 0.07 $g/cm^3$, and that the hydrodynamic friction coefficient of a cell is $6\pi\eta R$, where $\eta$ is the buffer viscosity (approximately 0.001 Pa, but may be higher with additive chemicals such as sucrose), the time to drop a distance of 25 microns is approximately 0.4 s. And the time for a typical salt ion, such as Na or K, to diffuse a distance of 25 microns is 0.6 s. This indicates that the flow layers remain laminar (and retain their respective conductivities) for the time it takes the cells to cross the electrode region when the patterned electrodes are about 2.5 cm by 0.5 cm in width and length.

Following the electroporation of a given volume of cells the electroporation efficiency and cell viability are determined by phase contrast and static fluorescent imaging, and sometimes by flow cytometry. After the cells are electroporated with the GFP-expressing plasmid in the flow chip, the cells are collected and transferred to a 96 or 24 well plate with appropriate cell medium, such as DMEM. The cells are cultured at 37° C. in an incubator with 5% $CO_2$ for 1, 6, 12, 24, or 48 hours. The cells are centrifuged at 300 g for 5 min and the aspirant is discarded. The cells are washed with PBS and this process is repeated. Following this, the cells are stained with propidium iodide (Invitrogen) at a concentration of approximately 1 microgram/mL. The cells are incubated in the dark for 15 min and then optically examined by phase contrast under fluorescent filters. A standard GFP filter set is used to determine the fraction of cells that have been electroporated with the plasmid. A filter set with excitation at 488 nm and emission at approximately 620 nm is used to determine the dead cells that have been permeated by propidium iodide. Several images can be acquired at different locations to improve the statistics of the electroporation efficiency and the cell viability. The cells may also be examined by flow cytometry to determine the fraction that has been electroporated as identified by a green fluorescent signal and the fraction that are dead as identified by uptake of propidium iodide and a red fluorescent signal.

Thus the described chip can reliably be used to electroporate a large number of mammalian or bacterial cells at high efficiency and with low cell death in a short amount of time. The cells can be transfected with plasmid DNA that can be transcribed into a protein that is therapeutic for a disease.

The cells can be transfected with mRNA that is likewise transcribed into a protein that is necessary for improving the health of the cell or that can be harvested for other medical use, such as production of antibodies. The cells can also be transfected with purified Cas9 protein, or another DNA guided nuclease, and synthetic guide RNA molecules, termed ribonucleoproteins, in order to efficiently edit a genomic site that is deleterious.

The method outlined in Example 1 can be used to electroporate a variety of different mammalian cell types including: CHO, Hela, T-cells, CD8+, CD4+, CD3+, PBMC, Huh-7, Renca, NIH 3T3, Primary Fibroblasts, hMSCs, K562, Vero, HEK 293, A549, B16, BHK-21, C2C12, C6, CaCo-2, CAP-T, COS-1, Cos-7, CV-1, DLD-1, H1299, Hep G2, HOS, Jurkat, L5278Y, LNCaP, MCF7, MDA-MB-231, MDCK, Mesenchymal Stem Cells, Min-6, Neuro2a, NIH3T3L1, NSO, Panc-1, PC12, PC-3, RBL, RLE, SF21, SF9, SH-SY5Y, SK-MES-1, SK-N-SH, SL3, SW403, THP-1, U20S, U937.

The method outlined in Example 1 can be used to electroporate a variety of different types of molecules to any mammalian cell including: DNA, RNA, mRNA, siRNA, miRNA, other nucleic acids, proteins, peptides, enzymes, metabolites, membrane impermeable drugs, cryoprotectants, exogenous organelles, molecular probes, nanoparticles, lipids, carbohydrates, small molecules, and complexes of proteins with nucleic acids (like CAS9-sgRNA). While the method outlined in Example 1 relies on an electric field to deliver charged nucleic acid molecules to electroporated cells, the method also suffices to electroporate neutral molecules where diffusive motion is sufficient for the delivery.

Although various embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed is:

1. A device capable of inserting a biologically active molecule into each of a plurality of living cells, comprising:
   a voltage controller;
   an upper chip extending along a first axis;
   a lower chip spaced from the upper chip, the lower chip extending along the first axis;
   a fluid channel formed between the upper chip and the lower chip, the fluid channel having a first end and a second end extending along the first axis therebetween, further comprising:
     a first fluid input formed in the upper chip perpendicular to the fluid channel and in fluid communication with the first end of the fluid channel;
     a second fluid input formed in the upper chip perpendicular to the fluid channel, the second fluid input spaced from the first fluid input along the first axis and in fluid communication with the fluid channel;
     a third fluid input formed in the lower chip opposite the second fluid input and perpendicular to the fluid channel, the third fluid input in fluid communication with the fluid channel; and
     a fluid output formed in the lower chip, the fluid output in fluid communication with the second end of the fluid channel;
   the fluid channel is configured to allow a fluid flow comprising the plurality of living cells and the biologically active molecule through the fluid channel; and
   a first electrode disposed on the upper chip and a second electrode disposed on the lower chip on opposite sides of the fluid channel to which electrical potentials are applied by the voltage controller to form an electric field directed across the fluid channel, wherein the first and second electrodes are separated by a first distance of about 50-100 micrometers which enables the plurality of living cells to pass through the space between the electrodes, and a second distance across the channel perpendicular to the first distance which enables the plurality of living cells to be more than one cell wide while it is flowing in the fluid channel, and the electric field is sufficient to form pores within the cell membrane of each of the plurality of living cells through which the biologically active molecule can traverse the cell membrane, but is not strong enough to lyse the plurality of living cells.

2. The device of claim 1, wherein the first and second electrodes comprise electrically conducting layers; and the first and second electrodes are disposed on opposite sides of the fluid channel.

3. The device of claim 2, wherein the upper chip, the lower chip, the fluid channel and the electrodes comprise an optically transparent material to allow observation of the motion of the living cells in the fluid channel of the device.

4. The device of claim 3, wherein the electrodes are patterned to create spatially varying electric fields or the applied electrical potential is held constant in time or pulsed.

5. The device of claim 4, wherein the applied electrical potential is pulsed, and pulse duration is about 0.01 millisec to about 100 millisec.

6. The device of claim 3, wherein the dimensions of the channel are varied; and the velocity of the fluid flow containing cells varies as a function of the first and second distances of the channel.

7. The device of claim 2, wherein the electrodes are patterned to create spatially varying electric fields or the applied electrical potential is held constant in time or pulsed.

8. The device of claim 7, wherein the applied electrical potential is pulsed, and pulse duration is about 0.01 millisec to about 100 millisec.

9. The device of claim 2, wherein the dimensions of the channel are varied; and the velocity of the fluid flow containing cells varies as a function of the first and second distances of the channel.

10. The device of claim 1, wherein the upper chip, the lower chip, the fluid channel and the electrodes comprise an optically transparent material to allow observation of the motion of the living cells in the fluid channel of the device.

11. The device of claim 1, wherein the electrodes are patterned to create spatially varying electric fields or the applied electrical potential is held constant in time or pulsed.

12. The device of claim 11, wherein the applied electrical potential is pulsed, and pulse duration is about 0.01 millisec to about 100 millisec.

13. The device of claim 1, wherein the dimensions of the channel are varied; and the velocity of the fluid flow containing cells varies as a function of the first and second distances of the channel.

14. The device of claim 1, wherein the fluid flow comprises a first solution comprising the plurality of living cells, and a second solution comprising the biologically active molecules.

15. The device of claim 14, wherein the first solution flows into the fluid channel through the first fluid input.

16. The device of claim 15, wherein the second solution flows into the fluid channel through the second fluid input and the third fluid input.

17. The device of claim 16, wherein the first solution flows through the fluid channel sheathed on opposite sides by the second solution.

* * * * *